(12) United States Patent
Guillon et al.

(10) Patent No.: US 8,791,313 B2
(45) Date of Patent: Jul. 29, 2014

(54) PROCESS FOR ISOMERIZING AN AROMATIC C8 CUT

(75) Inventors: Emmanuelle Guillon, Vourles (FR); Christophe Bouchy, Lyons (FR); Eric Sanchez, Saint Genis Laval (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 161 days.

(21) Appl. No.: 13/530,186

(22) Filed: Jun. 22, 2012

(65) Prior Publication Data
US 2012/0330077 A1    Dec. 27, 2012

(30) Foreign Application Priority Data

Jun. 24, 2011 (FR) ..................... 11 01963

(51) Int. Cl.
*C07C 5/27* (2006.01)
*B01J 29/74* (2006.01)
*B01J 37/20* (2006.01)
*B01J 35/00* (2006.01)
*B01J 37/16* (2006.01)

(52) U.S. Cl.
CPC ........... *C07C 5/2775* (2013.01); *B01J 29/7446* (2013.01); *B01J 37/20* (2013.01); *B01J 2229/20* (2013.01); *C07C 2529/72* (2013.01); *B01J 35/0066* (2013.01); *B01J 37/16* (2013.01); *B01J 2229/42* (2013.01)

USPC ....................... 585/481; 585/482; 585/480

(58) Field of Classification Search
USPC ........................................ 585/481, 482, 480
See application file for complete search history.

(56) References Cited

U.S. PATENT DOCUMENTS 6,512,155 B1    1/2003    Johnson et al.
6,635,791 B1    10/2003   Magne-Drisch et al.

OTHER PUBLICATIONS

F. Moreau et al., "Ethylbenzene Isomerization Over Bifunctional Platinum Alumina—EUO Catalysts: Location of the Active Sites", Microporous and Mesoporous Materials, vol. 90, No. 1-3 (2006) pp. 327-338.
P. Moreau et al., "Influence of Zeolite Structure on Ethylbenzene Transformation", Zeolites and Related Materials: Trends, Targets and Challenges, Part B Proceedings of the 4$^{th}$ International FEZA Conference, vol. 174B (Jan. 1, 2008) pp. 1179-1182.

*Primary Examiner* — Thuan D Dang
(74) *Attorney, Agent, or Firm* — Millen, White, Zelano & Branigan, P.C.

(57) ABSTRACT

The invention concerns a process for the isomerization of aromatic compounds containing 8 carbon atoms per molecule in the presence of a catalyst comprising at least one zeolite with structure type EUO, wherein said process is operated in the presence of water in the feed at the end of a catalyst activation period.

10 Claims, 1 Drawing Sheet

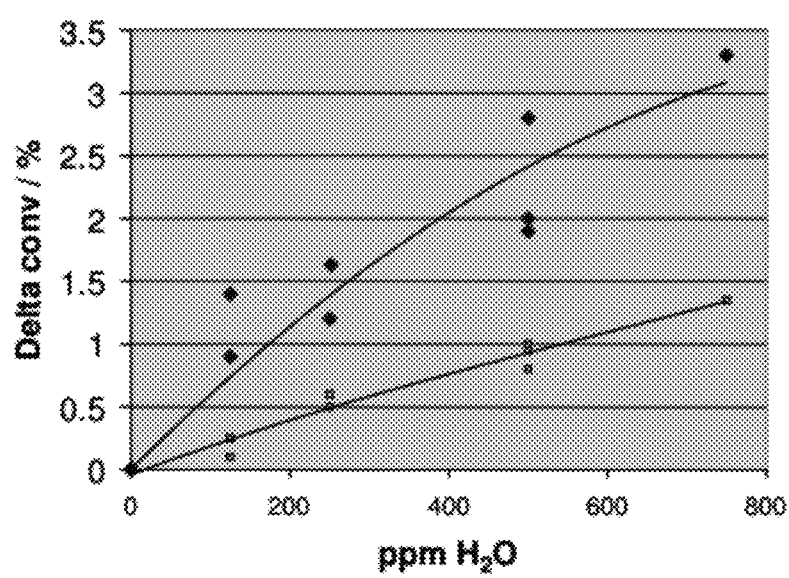

ial C8 cut (aromatic com-

PROCESS FOR ISOMERIZING AN AROMATIC C8 CUT

FIELD OF THE INVENTION

The present invention relates to a process for the isomerization of aromatic compounds containing 8 carbon atoms per molecule in the presence of a catalyst comprising at least one zeolite with structure type EUO, wherein said process is operated in the presence of water in the feed at the end of a catalyst activation period. In particular, the present invention is applicable to the isomerization of aromatic compounds containing 8 carbon atoms per molecule into para-xylene, and more particularly to the isomerization of ethylbenzene into para-xylene.

PRIOR ART

The isomerization of an aromatic C8 cut (aromatic compounds containing 8 carbon atoms per molecule) is the principal pathway to the formation of para-xylene, a highly sought-after product in the petrochemicals industry, used in particular for the manufacture of polyester fibres and films. The aromatic C8 cut from catalytic reforming or steam cracking comprises meta-, para-, ortho-xylene and ethylbenzene. The cost of separating ethylbenzene by distillation is too high, and so only the para-xylene and possibly ortho-xylene are separated by selective separation on zeolites using various separation processes. The residual C8 cut is then transformed in an isomerization unit, with the aim of maximizing the fraction of para-xylene and of upgrading the ethylbenzene to xylenes or benzene.

The isomerization of xylenes occurs using a mono-functional acid mechanism, the acid function generally being provided by a zeolite. In contrast, the transformation of ethylbenzene necessitates a bifunctional catalyst having both an acid function and a hydrogenating function. In existing processes, ethylbenzene is either isomerized to xylenes or dealkylated to benzene. These are thus known as either isomerizing isomerization or dealkylating isomerization.

The catalysts employed are generally bifunctional catalysts combining a zeolitic phase, at least one metal and a binder.

Among the zeolites used for the isomerization of aromatic C8 cuts is ZSM-5, alone or as a mixture with other zeolites such as mordenite, for example. Such catalysts have been described in particular in U.S. Pat. No. 4,467,129, U.S. Pat. No. 4,482,773 and EP-B-138617. Other catalysts are based on mordenite and have been described, for example, in U.S. Pat. No. 4,723,051, U.S. Pat. No. 4,665,258 and FR-A-2 477 903.

Application US 2005/0277796 and U.S. Pat. No. 6,388, 159, U.S. Pat. No. 6,313,363 may also be cited; they use zeolitic catalysts of the MTW or EUO type.

An improvement to zeolitic catalysts in isomerizing isomerization to xylenes would consist of increasing the conversion of ethylbenzene, the most difficult step in this transformation. In particular, secondary side reactions such as disproportionation and dealkylation of ethylbenzene limit upgrading of this compound to xylenes.

One pathway consists of modifying the catalyst by the nature of the zeolite used or by adding different metals. Another pathway consists of adjusting the operation of the process.

Certain processes function with a dry aromatic feed which is completely free of water, such as in U.S. Pat. No. 3,856, 872. In contrast, U.S. Pat. No. 4,723,050 teaches that adding a large quantity of water to the feed in isomerizing isomerization processes can limit coking of the catalyst.

U.S. Pat. No. 3,200,162 describes a process for the isomerization of xylenes without ethylbenzene in the presence of a catalyst based on silica-alumina free of metal with the addition of water to the feed. In document U.S. Pat. No. 6,512, 155, introducing traces of water into an isomerization process on a catalyst based on a zeolite of the MFI, FER, MWW, MEL or MTT type can reduce losses and improve the service life of the catalyst.

The effect of adding water to the feed thus depends on a plurality of parameters, such as the type of process (isomerizing or dealkylating), the type of feed and the catalyst employed.

The Applicant has discovered a process for the isomerizing isomerization of an aromatic C8 cut comprising at least ethylbenzene in the presence of a catalyst based on an EUO type zeolite, wherein adding a small quantity of water to the feed to be treated after a step for activation of said catalyst can improve the conversion of ethylbenzene.

SUMMARY AND ADVANTAGE OF THE INVENTION

The invention consists of a process for the isomerizing isomerization of an aromatic C8 cut containing at least ethylbenzene employing a catalyst based on an EUO type zeolite during which water is introduced in a quantity in the range 50 ppm to 8000 ppm at the end of a catalyst activation phase.

BRIEF DESCRIPTION OF FIG. 1

FIG. 1 represents the catalytic performances of a catalyst A in the isomerization of an aromatic C8 cut used in accordance with the process of the invention (♦) with respect to an operation not in accordance with the process of the invention (■), measured as the delta conversion (%) up the ordinate as a function of the water content in the feed, along the abscissa. The delta conversion corresponds to the conversion of ethylbenzene, as the difference between the conversion measured in the presence of water and in the absence of water in the feed.

DETAILED DESCRIPTION OF THE INVENTION

The invention consists of a process for the isomerizing isomerization of an aromatic C8 cut containing at least ethylbenzene employing a catalyst based on EUO type zeolite, during which water is introduced in a quantity in the range 50 ppm to 8000 ppm at the end of a catalyst activation phase.

The process of the present invention employs a prior activation step carried out under more severe conditions than the isomerization conditions proper, in order to coke the catalyst. At the end of this activation step, the coke content on the catalyst, measured by carbon analysis of the discharged catalyst and after Soxhlet extraction with toluene is advantageously in the range 0.5% to 4% by weight, preferably in the range 0.8% to 3% by weight with respect to the total catalyst mass.

The process of the present invention can be used to obtain improved ethylbenzene conversions while maximizing the para-xylene-rich fraction. Another advantage of the process of the invention is a gain in the stability of the catalyst in the process of the invention.

The present invention pertains to a process for the isomerizing isomerization of a feed comprising aromatic compounds containing 8 carbon atoms per molecule and at least ethylbenzene, in the presence of a catalyst comprising at least one zeolite with structure type EUO at least partially in the acid form, at least one metal from group VIII of the periodic classification of the elements, and at least one binder, said process comprising:

a) reducing the catalyst;
b) activating the catalyst by bringing said catalyst into the presence of said feed;
c) introducing water into said feed in a quantity in the range 50 ppm to 8000 ppm;
d) bringing the feed containing water from step c) into contact with the catalyst activated in step b) under isomerization conditions.

The catalyst used in the process of the present invention is employed in reactions for the isomerization of a feed comprising aromatic compounds containing 8 carbon atoms per molecule and at least ethylbenzene. Advantageously, said feed comprises ethylbenzene alone. Preferably, it comprises a mixture of xylene(s) and ethylbenzene.

The feed to be treated used in the present invention may contain paraffins containing 8 carbon atoms as well as naphthenes containing 8 carbon atoms. Preferably, said feed comprising aromatic compounds containing 8 carbon atoms per molecule and at least ethylbenzene originates from catalytic reforming or steam cracking.

In the context of the present invention, the aromatic feed, the feed or the aromatic C8 feed are intended to correspond to a hydrocarbon feed comprising at least aromatic compounds containing 8 carbon atoms per molecule and at least ethylbenzene.

The water content of the feed used in the process of the present invention is generally in the range 0 to 200 ppm by weight, preferably in the range 0 to 150 ppm by weight, and more preferably in the range 0 to 50 ppm by weight.

After the steps for reduction and preferred sulphurization of the catalyst, the catalyst undergoes an activation step (step b). The aromatic feed is introduced under the following operating conditions:

a temperature in the range 450° C. to 600° C., limits included, preferably in the range 500° C. to 600° C., limits included, more preferably in the range 530° C. to 600° C., limits included;
a partial pressure of hydrogen (ppH$_2$) in the range 2 to 45 bar, limits included, (1 bar=0.1 MPa), preferably in the range 10 bar to 45 bar, limits included, more preferably in the range 10 to 40 bar, limits included;
a total pressure in the range 5 to 50 bar, limits included, preferably in the range 10 to 45 bar, limits included;
a space velocity, expressed in kilogram of feed introduced per kilogram of catalyst per hour (WHSV) in the range 0.25 to 30 h$^{-1}$, limits included, preferably 1 to 10 h$^{-1}$, limits included, and more preferably in the range 2 to 6 h$^{-1}$, limits included.

Preferably, the activation step is carried out for a duration in the range 10 hours to 500 hours, preferably in the range 10 hours to 200 hours.

Before the isomerization step, step c) of the process of the invention corresponds to introducing water in an amount by weight of water with respect to the feed in the range 50 ppm to 8000 ppm, preferably in the range 50 ppm to 800 ppm, preferably in the range 150 ppm to 1000 ppm.

After the catalyst activation step (step b), and after the water has been introduced in the defined quantities (step c), the feed comprising the aromatic compounds containing 8 carbon atoms per molecule and at least ethylbenzene is introduced into an isomerization unit under the conditions of an isomerization process, which conditions are milder than the activation conditions, namely:

a temperature of 400° C. or less, preferably 395° C. or less, preferably in the range 0° C. to 395° C., preferably in the range 100° C. to 395° C.;
a partial pressure of hydrogen, ppH$_2$, of 20 bar or less, preferably 10 bar or less, preferably in the range 0 to 20 bar, preferably in the range 0 to 10 bar;
a total pressure of 30 bar or less, preferably 25 bar or less, preferably in the range 0 to 30 bar, preferably in the range 0 to 25 bar;
a space velocity, expressed in kilograms of feed introduced per kilogram of catalyst per hour (WHSV) of 30 h$^{-1}$ or less, preferably in the range 0 to 30 h$^{-1}$;
a quantity by weight of water added with respect to the feed in the range 50 ppm to 8000 ppm, preferably in the range 50 ppm to 800 ppm, preferably in the range 150 ppm to 1000 ppm.

Advantageously, the conditions of step d) of the isomerization process are as follows:

a temperature in the range 300° C. to 400° C., limits included, preferably in the range 320° C. to 400° C., limits included, and more preferably in the range 340° C. to 400° C., limits included;
a partial pressure of hydrogen, ppH$_2$, in the range 2 to 20 bar, limits included, preferably in the range 4 bar to 10 bar, limits included, more preferably in the range 5 to 10 bar, limits included;
a total pressure in the range 5 to 30 bar, limits included, preferably in the range 7 to 25 bar, limits included;
a space velocity, expressed in kilogram of feed introduced per kilogram of catalyst per hour (WHSV) in the range 0.25 to 30 h$^{-1}$, limits included, preferably 1 to 10 h$^{-1}$, limits included, and more preferably in the range 2 to 6 h$^{-1}$, limits included;
a quantity by weight of water added with respect to the feed in the range 50 ppm to 8000 ppm, preferably in the range 50 ppm to 800 ppm, preferably in the range 150 ppm to 1000 ppm.

The water added to the feed may be introduced upstream of the catalytic bed with the feed itself or indeed at any level of the catalytic bed. Preferably, the water is injected in the vapour form or such that it is in the vapour form in contact with the catalyst.

The feed used to activate the catalyst and that to be processed under the isomerization conditions" as used in the context of the present invention is intended to mean either different or identical feeds. Preferably, the two feeds are the same. In other words, the feed used in the activation step is the same as the feed used in the isomerization step proper.

In an industrial facility, the effluent from the reaction section of the isomerization unit generally undergoes one or more cooling steps in succession then separation in a flash drum generally known as a separator drum. The gas phase from said drum is recycled to the reaction section using a recycle compressor and constitutes the recycle. The liquid phase from said drum is generally sent to one or more distillation separation columns in order, if necessary, to recycle a naphthene cut to the reaction section and to separate the light products or by-products of the reaction such as benzene, toluene and C8+ aromatics (aromatics containing more than 8 carbon atoms).

After the activation step b), and in order to maintain a partial pressure of water over the catalyst, the water is injected into the system in a number of different manners.

A first method consists of injecting steam into the recycle gas in order to provide the desired water content, i.e. a quantity by weight of water with respect to the feed in the range 50 ppm to 8000 ppm, preferably in the range 50 ppm to 800 ppm, preferably in the range 150 ppm to 1000 ppm.

A second method consists of injecting a small quantity of liquid water, advantageously in the range 50 to 7800 ppm, into the feed and sending the mixture obtained to the inlet to the isomerization unit or units; the water which is dissolved or free in the isomerization feed is then transformed into steam in the various heat exchange systems or ovens of the isomerization reaction unit, thus allowing the optimal concentration mentioned in the present description to be obtained.

A third method consists of injecting with the feed any other products known to the skilled person which are compatible with the process (i.e. not deleterious to the reaction system), which decompose into water under the operating conditions for isomerization. Alcohols may be cited by way of example, such as methanol or ethanol, for example.

The catalyst used in the process of the invention contains an EUO type zeolite, preferably a zeolite selected from the group constituted by zeolites EU-1, ZSM-50 and TPZ-3, more preferably from the group constituted by EU-1 and ZSM-50 zeolites; more preferably, the zeolite is EU-1 zeolite.

The zeolite with structure type EUO contained in the catalyst, in particular EU-1 zeolite, ZSM-50 zeolite or TPZ-3 zeolite, and their production process are described in the literature, for example in patents EP B1 42 226, U.S. Pat. No. 4,640,829 or EPA 51318.

The catalyst used in the process of the invention comprises:
at least one zeolite with structure type EUO;
at least one metal from group VIII of the periodic classification of the elements (corresponding to groups 8 to 10 of the new periodic classification of the elements, CRC Handbook of Chemistry and Physics, 2000-2001);
at least one binder.

More precisely, the catalyst used in the process of the invention is advantageously composed of:
1% to 90%, limits included, preferably 3% to 60%, limits included, and more preferably 4% to 40%, limits included, by weight of at least one zeolite with structure type EUO comprising silicon and at least one element T selected from the group formed by aluminium, iron, gallium and boron, with an atomic ratio Si/T in the range 5 to 100, limits included, preferably in the range 5 to 80, limits included, and more preferably in the range 5 to 50, limits included. Preferably, said element T is selected from the group constituted by aluminium and boron; more preferably, the element T is aluminium;
0.01% to 2%, limits included, preferably 0.05% to 1.0%, limits included, by weight, of at least one metal from group VIII of the periodic classification of the elements, said metal from group VIII being deposited on the zeolite or on the binder;
the complement to 100% by weight of at least one binder.

Advantageously, said catalyst used in the process of the invention contains EU-1 zeolite.

Preferably, the metal from group VIII of the periodic classification of the elements comprised in the catalyst used in the process of the invention is a metal selected from the group constituted by palladium and platinum, preferably platinum.

Said zeolite with structure type EUO comprised in the catalyst used in the process of the invention is at least partially in the acid form, i.e. in the hydrogen form (H), the atomic ratio C/T being less than 0.5, preferably less than 0.15; the competing cation C being selected from the group constituted by alkali or alkaline-earth cations, preferably from the group constituted by the cations $Na^+$ and $K^+$; preferably, the competing cation C is the cation $Na^+$. Advantageously, the zeolite in the (H) form is such that the atomic ratio Na/Al is less than 0.5, preferably less than 0.15.

In a variation of the invention, the catalyst used in the process of the invention may also comprise:
0.01% to 2%, limits included, preferably 0.05% to 1.0%, limits included, by weight of at least one metal from the group formed by the groups IIIA and IVA of the periodic classification of the elements (corresponding to groups 3 and 4 of the new periodic classification of the elements), preferably selected from the group formed by tin and indium;
optionally, sulphur, the quantity of which is such that the ratio of the number of sulphur atoms to the number of deposited metal atoms from group VIII is in the range 0.1 to 2, limits included;
the complement to 100% by weight of at least one binder.

Any zeolite with structure type EUO known to the skilled person would be suitable for the catalyst used in the process of the present invention. Thus, for example, the zeolite used as a base to prepare said catalyst may be as-synthesized EU-1 zeolite with the required specifications as regards the Si/T ratio defined above, and more particularly the Si/Al ratio described above.

The present invention includes any type of dealumination treatment for the zeolite used in the process of the invention which is known to the skilled person, for example a steaming treatment, i.e. heat treatment in the presence of water, or acid attack.

The binder (or matrix) included in the catalyst used in the process of the present invention generally consists of at least one element selected from the group formed by clays, magnesia, aluminas, silicas, titanium oxide, boron oxide, zirconia, aluminium phosphates, titanium phosphates, zirconium phosphates and silica-aluminas. Charcoal may also be used. Preferably, the binder used in the catalyst used in the process of the invention is alumina. Any alumina which is known to the skilled person, with various specific surface areas and pore volumes, may be suitable for the catalyst of the process of the invention, preferably a gamma type alumina with a specific surface area in the range 100 to 250 $m^2/g$.

The metals may be introduced either in the same manner or using different techniques, at any time of the preparation, before or after shaping and in any order. Furthermore, intermediate treatments such as calcining and/or reduction, for example, may be applied between the deposits of the various metals.

The catalyst used in the present invention, of at least one noble metal from the platinum family, is advantageously employed by using compounds in the ammoniacal or acid form. In this case, the noble metal is deposited on the zeolite.

The platinum is generally introduced into the matrix in the form of hexachloroplatinic acid, but any ammoniacal compound of an noble metal may also be used, or compounds such as, for example, ammonium chloroplatinate, platinum dicarbonyl dichloride, hexahydroxyplatinic acid, palladium chloride or palladium nitrate.

In the case of platinum, it is also possible to cite the use of tetramine platinum II salts with formula $Pt(NH_3)_4X_2$, hexamine platinum IV salts with formula $Pt(NH_3)_6X_4$; halogenopentamine platinum IV salts with formula $(PtX(NH_3)_5)X_3$; tetrahalogenodiamine platinum IV salts with formula $PtX_4(NH_3)_2$; platinum complexes with halogen-polyketones and halogen compounds with formula $H(Pt(acac)_2X)$; X being a halogen selected from the group formed by chlorine, fluorine, bromine and iodine; preferably, X is chlorine, and acac represents the acetylacetonate group, $C_5H_7O_2$, derived from acetylacetone.

The additional metal selected from the group formed by elements from groups IIIA and IVA may be introduced via compounds such as, for example, chlorides, bromides or nitrates of alkyls of elements from groups IIIA and IVA, i.e. preferably, tin or indium, alkyl tin and indium nitrate or chloride. Preferably, the tin is introduced during shaping of the zeolite with the binder.

The catalyst may be prepared using any method known to the skilled person.

Preferably, calcining is carried out, then at least one ion exchange in at least one solution of $NH_4NO_3$ so as to obtain a zeolite with an atomic ratio C/T of less than 0.5, preferably less than 0.15. Advantageously, the competing cation C is the cation $Na^+$ and the element T is aluminium.

The ion exchange is preferably carried out in the presence of ammonium nitrate or ammonium acetate in a concentration of 0.005 to 15 N, preferably 0.1 to 10 N, at a temperature in the range 15° C. to 100° C., for a period of 1 to 10 hours in a batch or continuous reactor. In general, after the exchange step, the zeolite obtained is dried, for example in an oven, at a temperature in the range from ambient temperature to 250° C., before being calcined at a temperature in the range 300° C. to 600° C. in air. It is possible to carry out successive exchanges.

Next, the catalyst used in the present invention is generally shaped such that the catalyst is preferably in the form of extrudates or beads for use in the process of the invention. In a variation of the preparation of the catalyst, shaping is carried out before calcining and ion exchange.

Preparation of the catalyst is advantageously completed by calcining, normally at a temperature in the range 250° C. to 600° C., limits included, for a period of approximately 0.5 to 10 hours. Preferably, calcining is preceded by drying, for example oven drying, at a temperature in the range from ambient temperature to 250° C., preferably in the range 40° C. to 200° C., limits included. Said drying step is preferably carried out during the temperature rise necessary to carry out said calcining.

In a preferred implementation of the process of the invention, the catalyst used undergoes a steaming step after calcining, i.e. a step for heat treatment in the presence of water.

In a variation of the invention, the catalyst used in the process of the present invention contains sulphur. The sulphur is introduced onto the shaped, calcined catalyst containing the metal or metals cited above, either in situ or ex situ before the activation step and the isomerization step proper. In the case of in situ sulphurization, if the catalyst used in the process of the present invention has not previously been reduced, reduction occurs before sulphurizing. In the case of ex situ sulphurization, reduction is carried out followed by sulphurization. Sulphurization is carried out in the presence of hydrogen using any sulphurizing agent which is well known to the skilled person, such as dimethyl sulphide, dimethyldisulphide or hydrogen sulphide. As an example, said catalyst is treated with a feed containing dimethyldisulphide, $(CH_3)_2S_2$, in the presence of hydrogen in a concentration such that the sulphur/metal atomic ratio is 1.5. The catalyst is then maintained for approximately 3 hours at approximately 400° C. in a flow of pure hydrogen before injecting the feed corresponding to the activation step of the process of the present invention.

Irrespective of the implementation of the preparation of the catalyst to be used in the process of the invention, prior reduction of the final catalyst may be carried out ex situ in a stream of hydrogen, for example at a temperature in the range 450° C. to 600° C., for a period in the range 0.5 to 4 hours.

In the case in which the catalyst does not contain sulphur, reduction of the metal is carried out in hydrogen in situ before injecting the feed corresponding to the activation step of the process of the present invention.

The following examples illustrate the invention without in any way limiting its scope.

Example 1

Preparation of Catalyst a Containing EU-1 Zeolite and 0.3% by Weight of Platinum The starting material used was an as-synthesized EU-1 zeolite comprising the organic template, silicon and aluminium, having an Si/Al atomic ratio of 15 and a sodium content with respect to the weight of dry EU-1 zeolite of 1.5% by weight, corresponding to a Na/Al atomic ratio of 0.4.

This EU-1 zeolite initially underwent calcining at 550° C. in a stream of air for 6 hours. Next, the solid obtained underwent three ion exchange steps in a 10 N solution of $NH_4NO_3$ at approximately 100° C. for 4 hours for each exchange step.

At the end of these treatments, the EU-1 zeolite in the $NH_4$ form had a Si/Al overall atomic ratio of 15 and a sodium content with respect to the weight of dry EU-1 zeolite of 50 ppm, corresponding to a Na/Al atomic ratio of 0.003.

The EU-1 zeolite was then shaped by extrusion with an alumina gel to obtain, after drying and calcining in dry air, a support constituted by extrudates 1.4 mm in diameter, which contained approximately 10% by weight of EU-1 zeolite in the H form and approximately 90% alumina.

The support obtained underwent anionic exchange with hexachloroplatinic acid in the presence of a competing agent (hydrochloric acid) in order to deposit 0.3% by weight of platinum with respect to the catalyst. The moist solid was then dried at 120° C. for 12 hours and calcined in air at a temperature of 500° C. for one hour.

The catalyst obtained contained 10.0% by weight of EU-1 zeolite in the hydrogen form (H), 89.7% of alumina and 0.3% of platinum. The dispersion of the platinum, measured by oxygen chemisorption, was 90%.

Example 2

Evaluation of Catalytic Properties of Catalyst a in the Isomerization of an Aromatic C8 Cut Using the Process of the Invention The performance of catalyst A was evaluated by means of the isomerization of an aromatic C8 cut principally containing meta-xylene, ortho-xylene and ethylbenzene. The operating conditions were as follows:

| Feed | % by weight |
|---|---|
| Naphthenes N8 | 3.1 |
| Toluene | 0.2 |
| Ethylbenzene | 12.9 |
| Ortho-xylene | 18.5 |
| Meta-xylene | 60.4 |
| Para-xylene | 4.9 |
| $H_2O$ | 22 ppm |

The catalyst was held for 3 hours at 400° C. in a stream of pure hydrogen, then the feed was injected.

In one case (not in accordance with the invention), the aromatic feed was directly injected onto the catalyst A under the following conditions: 385° C., WHSV=3.5 h$^{-1}$ (mass of feed/mass of catalyst/hour), total pressure=10 bar, ppH$_2$=8.8 bar.

In a second case (in accordance with the invention), the catalyst underwent an activation step for 80 hours in the feed at 480° C., WHSV=3 h$^{-1}$, a total pressure of 15 bar and a partial pressure of hydrogen, ppH$_2$=8.8 bar, then the operating conditions were adjusted to those of the case which was not in accordance: 385° C., WHSV=3.5 h$^{-1}$, total pressure=10 bar, ppH$_2$=8.8 bar.

In both cases, the effect of adding water to the feed on the ethylbenzene conversion was measured for various quantities of water added under the same operating conditions: 385° C., WHSV=3.5 h$^{-1}$, total pressure=10 bar, ppH$_2$=8.8 bar.

The catalysts were compared by the ethylbenzene conversion, by difference between the conversion measured in the presence of water and in the absence of water in the feed (FIG. 1).

The catalyst which had undergone activation before introducing the feed containing water exhibited an increase in the conversion of ethylbenzene to para-xylene (delta conversion) that was substantially higher than the catalyst which had not undergone the activation described above.

The entire disclosures of all applications, patents and publications, cited herein and of corresponding French application Ser. No. 11/01.963, filed Jun. 24, 2011 are incorporated by reference herein.

The preceding examples can be repeated with similar success by substituting the generically or specifically described reactants and/or operating conditions of this invention for those used in the preceding examples.

The invention claimed is:

1. A process for the isomerization of a feed comprising aromatic compounds containing 8 carbon atoms per molecule and at least ethylbenzene, in the presence of a catalyst comprising at least one zeolite with structure type EUO at least partially in acid form, at least one metal from group VIII of the periodic classification of the elements, and at least one binder, said process comprising:
   a) reducing the catalyst;
   b) activating the catalyst by bringing said catalyst into contact with said feed at a temperature in the range 450° C. to 600° C., limits included, a partial pressure of hydrogen in the range 2 to 45 bar, limits included, a total pressure in the range 5 to 50 bar, limits included, and at a space velocity in the range 0.25 to 30 h$^{-1}$, limits included;
   c) introducing water into said feed in a quantity in the range 50 ppm to 8000 ppm;
   d) bringing the feed containing water from step c) into contact with the catalyst activated in step b) under isomerization conditions.

2. A process according to claim 1, in which the catalyst in the acid form has an atomic ratio C/T of less than 0.5.

3. A process according to claim 1 in which the reduction of the catalyst in step a) is followed by a sulphurization step.

4. A process according to claim 1, in which said zeolite with structure type EUO is EU-1 zeolite.

5. A process according to claim 1, in which said zeolite with structure type EUO is ZSM-50 zeolite.

6. A process according to claim 1, in which said zeolite with structure type EUO is TPZ-3 zeolite.

7. A process according to claim 1, in which said catalyst further comprises at least one metal selected from metals from groups IIIA and IVA of the periodic classification of the elements.

8. A process according to claim 1, in which, at the end of activation step b), the quantity of coke on the catalyst is in the range 0.5% to 4% by weight with respect to the total catalyst mass.

9. A process according to claim 8, in which the quantity of coke is in the range 0.8% to 3% by weight with respect to the total catalyst mass.

10. A process according to claim 1, in which the isomerization conditions in step d) are a temperature of 400° C. or less, a partial pressure of hydrogen of 20 bars or less, a total pressure of 30 bars or less and a space velocity of 30 h$^{-1}$ or less.

* * * * *